United States Patent [19]

Graff et al.

[11] Patent Number: 4,922,899
[45] Date of Patent: May 8, 1990

[54] DOUBLE-COVERAGE ATHLETIC PROTECTIVE CUP WITH HINGED FLANGE

[76] Inventors: Jeffrey J. Graff; Deanna M. Graff, both of 7930 NW. 21 St., Sunrise, Fla. 33322

[21] Appl. No.: 274,365

[22] Filed: Nov. 21, 1988

[51] Int. Cl.$^5$ .............................................. A61F 5/40
[52] U.S. Cl. .................................. 128/158; 128/159; 128/846; 2/2
[58] Field of Search ............... 128/158, 159, 160, 161, 128/168, 846, 845, 885, 876; 2/2, 401, 403, 405

[56] References Cited

U.S. PATENT DOCUMENTS

| 1,830,572 | 11/1931 | Taylor . | |
| 1,972,275 | 9/1934 | Record | 128/158 |
| 2,283,684 | 5/1942 | Matthews . | |
| 3,176,686 | 4/1965 | Barnes | 2/2 |
| 3,314,422 | 4/1967 | Phillips | 128/158 |
| 3,621,846 | 11/1971 | Lehman . | |
| 4,257,414 | 3/1981 | Gamm et al. . | |
| 4,295,227 | 10/1981 | Michell | 2/2 |
| 4,453,541 | 6/1984 | Castelli et al. . | |
| 4,471,772 | 9/1984 | Miller, Jr. | 128/159 |

Primary Examiner—Richard J. Apley
Assistant Examiner—Paul Prebilic
Attorney, Agent, or Firm—Leon Gilden

[57] ABSTRACT

An athletic protective cup apparatus is set forth to enclose the genitals of a user of the device comprising a first interiorly positioned cup device utilizing a central protective cup of a first hardness provided with an enlarged orthogonally oriented flange area extending outwardly of the cup to protect the abdomen and pelvic region of a wearer elastically secured to a wearer by a plurality of elastic straps. A second cup of a less dense and softer material of a second hardness less than the first hardness overlies the first cup and is secured to the flange portion of the first cup and further includes an elastic ring at a lowermost portion of the second cup to enable pivotal movement of the second cup relative to the first cup and enable ambulatory freedom of a wearer.

7 Claims, 1 Drawing Sheet

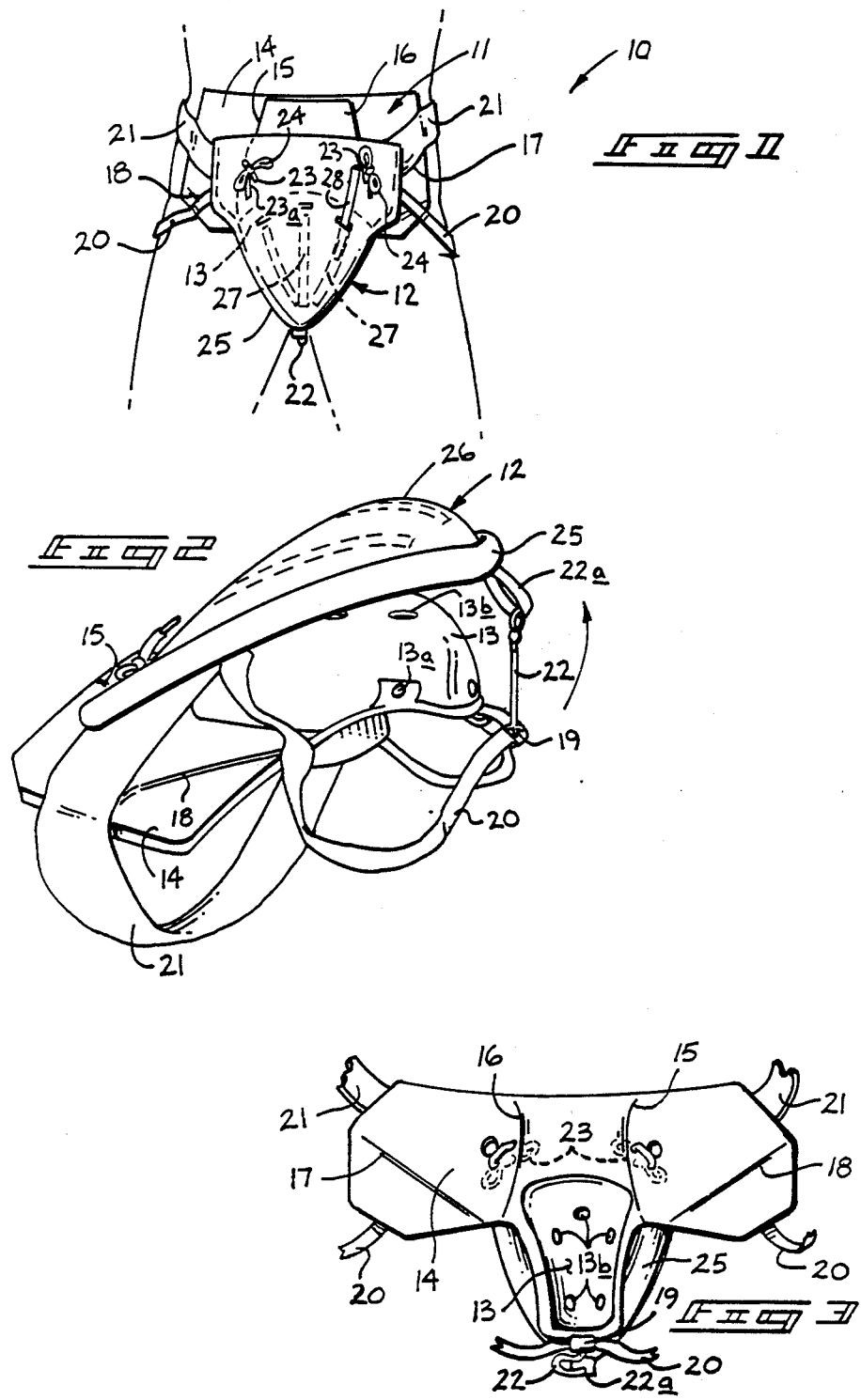

DOUBLE-COVERAGE ATHLETIC PROTECTIVE CUP WITH HINGED FLANGE

BACKGROUND OF THE INVENTION

1. Field of the Invention

The field of invention relates to protective athletic devices, and more particularly pertains to a double-coverage athletic protective cup wherein the same sets forth a plurality of relatively movably mounted cup devices of first and second durometer hardnesses to accommodate strikes to the groin and associated pelvic region of a wearer.

2. Description of the Prior Art

The use of protective athletic cup devices is well known in the prior art. While prior devices have attempted to fully protect the relatively sensitive groin region of a male wearer of the device, the prior art has failed to provide the plural cup construction utilizing varying hardness polymeric materials to provide protection of a wearer. For example, U.S. Pat. No. 1,830,572 to Taylor sets forth an interior cup 5 utilizing an exterior diaphragm to maintain a pressurized pneumatic chamber forwardly of the cup to soften strikes aimed at a groin area of a wearer.

U.S. Pat. No. 2,283,684 to Matthews sets forth an athletic protective cup wherein a cup is formed with a rearwardly directed perimeter cushioning member to provide a first spaced protective shock absorbing contact area with a wearer to enhance comfort and effectiveness of the cup, as opposed to the instant invention providing a plurality of protective cup portions, and further including a third protective means utilizing insertable strips to enhance the rigidity of the external cup as desired.

U.S. Pat. No. 3,621,846 to Lehman sets forth a male under garment provided with a plurality of layers including a forwardly directed support pouch and a flap disposed forwardly of the pouch to provide a plurality of protective areas relative to a groin portion of a wearer.

U.S. Pat. No. 4,257,414 to Gamm sets forth a protective cup device utilizing a rigid cup to enclose the genitals of a wearer and forwardly including a resilient molded portion positioned about the peripheral edge of the cup to enhance comfort of the cup, as utilized by a wearer.

U.S. Pat. No. 4,453,541 to Castelli sets forth a somewhat rigid cup positioned within a downwardly directed outer flap to secure the rigid cup to protect the groin area of a wearer.

As such, it may be appreciated that there continues to exist a need for a double-coverage athletic protective cup as set forth by the instant invention to address both the problems of effectiveness and comfort in use, and in this respect the present invention substantially fulfills this need.

SUMMARY OF THE INVENTION

In view of the foregoing disadvantages inherent in the known types of athletic protective cup devices now present in the prior art, the present invention provides a double-coverage athletic protective cup wherein the same provides for an interior cup including a pelvic protective portion with a second exterior cup of a reduced hardness securely fastened to the outer surface of the first cup and further provided with insertable flexible elongate members to vary the rigidity of the exterior cup, as desired. As such, the general purpose of the present invention, which will be described subsequently in greater detail, is to provide a new and improved double-coverage athletic protective cup which has all the advantages of the prior art athletic cup devices and none of the disadvantages.

To attain this, the present invention comprises a double-coverage athletic protective cup provided with a first relatively rigid cup-shaped member formed with an outwardly directed flange to overlie the pelvic and lower abdomen region of a wearer and wherein a further protective cup is secured to an exterior surface of the first cup and is pivotally mounted thereto at a lowermost portion to enable ambulatory mobility of a user. Further, insertable rigid modification devices comprising elongate strips are selectively insertable into the second cup to modify the hardness of the second cup to accommodate strikes of various severity. The second protective cup is of generally softer material than the first cup to provide a first cushioning effect relative to the interior or first cup.

My invention resides not in any one of these features per se, but rather in the particular combination of all of them herein disclosed and claimed and it is distinguished from the prior art in this particular combination of all of its structures for the functions specified.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved double-coverage athletic protective cup which has all the advantages of the prior art athletic cup devices and none of the disadvantages.

It is another object of the present invention to provide a new and improved double-coverage athletic protective cup which may be easily and efficiently manufactured and marketed.

It is a further object of the present invention to provide a new and improved double-coverage athletic protective cup which is of a durable and reliable construction.

An even further object of the present invention is to provide a new and improved double-coverage athletic protective cup which is susceptible of a low cost of manufacture with regard to both materials and labor, and which accordingly is then susceptible of low prices of sale to the consuming public, thereby making such double-coverage athletic protective cups economically available to the buying public.

Still yet another object of the present invention is to provide a new and improved double-coverage athletic protective cup which provides in the apparatuses and methods of the prior art some of the advantages thereof, while simultaneously overcoming some of the disadvantages normally associated therewith.

Still another object of the present invention is to provide a new and improved double-coverage athletic protective cup provided with a plurality of cup members wherein the interior cup members are of relatively rigid material elastically secured to a wearer wherein the second cup is of a softer material pivotally mounted to the first cup and further provided with insertable strip portions to modify the rigidity of the outer cup as deemed necessary.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is an orthographic view taken in elevation of the instant invention.

FIG. 2 is an isometric illustration of the instant invention.

FIG. 3 is a rear elevation view of the instant invention.

DESCRIPTION OF THE PREFERRED EMBODIMENT

With reference now to the drawings, and in particular to FIGS. 1 to 3 thereof, a new and improved double-coverage athletic protective cup embodying the principles and concepts of the present invention and generally designated by the reference numeral 10 will be described.

More specifically, it will be noted that the double-coverage athletic protective cup apparatus 10 essentially comprises a first inner cup member 11 for use adjacent a pelvic and lower abdominal region of a wearer. The first inner cup member 11 includes an inner cup 13 of generally transverse and longitudinal cup shaped configuration tapered downwardly and of generally greater elongate dimension relative to a transverse dimensional width. The flange portion 14 integrally secured to the inner cup 13 is formed to the inner cup 13 at about an upper perimeter thereof wherein the flange portion extends laterally and upwardly of the inner cup 13. The inner cup 13 may be integrally formed to the flange 14 or formed as a separately removable member secured thereto by snap fasteners 13a, as illustrated.

The flange portion 14 is further formed with first and second junction hinges 15 and 16 formed generally transversely of the flange portion 14 originating at a width somewhat equal to the width of the inner cup 13 and tapering towards one another towards the upper terminal edge of the flange portion 14. A third and fourth junction hinge 17 and 18 are formed to the flange portion 14 somewhat longitudinally of the flange portion 14 and directed angularly upwardly wherein the various junctions hinges 15, 16, 17, and 18 enable accommodation of various body contours and use in conjunction with the flange portion 14 that is molded of a curvilinear configuration to accommodate a lower torso portion of a human anatomy.

A non-elastic first loop 19 is formed at a lowermost terminal end of the inner cup 13. The first loop 19 accepts a lower elastic strap 20 secured to the outer cup member 12 of the instant invention. An upper elastic band 21 if formed in a continuous loop about an upper portion of the outer cup member 12. The upper elastic band 21 is secured about the torso of a wearer and is positioned for securement above the buttocks region of the wear wherein the lower elastic strap 20 accommodates the lower limbs of the wearer therethrough and is guided and maintained in position relative to the inner cup member 11 by means of the first loop 19 guidingly securing the lower elastic strap 20 therethrough, as illustrated in FIG. 2 for example.

An elastic connector strap 22 secures the second outer cup member 12 by use of a non-elastic second loop 22a secured at a lower terminal end of the second cup member 12 wherein the second cup member 12 is secured to the first inner cup member 11 by means of rigid loops 23 integrally formed to the first inner cup member 11 extending through elongate slots 23a of a complementary opening to accept the rigid loops 23a therethrough wherein flexible cords 24 are thereby woven through the loops 23 and thereby secure the inner cup member to the outer cup member 12 at an uppermost portion thereof wherein the elastic connector strip 22 thereby enables pivotment of the outer cup member 12 about the uppermost portion thereof utilizing the rigid loops 23 secured through the elongate slots 23a as a pivot axis.

The outer cup member 12 is formed with a cushion perimeter 25 extending along the side and lowermost portions of the outer cup member 12 and is further formed with a series of three elongate pockets 27 extending downwardly of the outer cup member 12 merging at an apex towards the lowermost end of the outer cup member 12 proximate the elastic second loop 22a. The elongate pockets 27 accommodate elongate flexible strips 28 therein wherein the outer cup member 12 may thereby be provided with stiffening means to enhance selectively the rigidity of the outer cup member 12. The outer cup member 12 is of a softer less rigid material than the inner cup member 11 to provide a cushioning effect to a wearer thereof and is additionally covered with a fabric 26 to enhance securement of the elastic strap 20 and upper band 21 thereto.

The inner cup member 11 is of a configuration contour to fit the groin and pelvic regions as noted above as well as the lower abdominal region and in use, the outer cup member 12 may hang freely forwardly of the inner cup member 11 due to the upward attachment of the outer cup member 12 to the inner cup member 11 by means of the rigid loops 23 positioned through the elongate slots 23a in the outer cup member 12.

The second outer cup 12 is formed with an interior configuration of complementary geometrical configuration to the exterior configuration of the first inner cup member 11 to provide a compact inter-relationship to enable secure alignment and positioning of the outer cup member 12 relative to the inner cup member 11.

Accordingly, the manner of usage and operation of the instant invention should be understood from the above description and no further discussion relative to the manner of usage and operation of the instant invention shall be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by LETTERS PATENT of the United States is as follows:

1. A double-coverage athletic protective cup apparatus comprising,
   an inner relatively rigid cup member, and
   a flange portion extending laterally and upwardly of said inner cup member and fixedly secured thereto, and
   an outer relatively soft cup member pivotally secured to said inner cup member, and
   an upper continuous elastic band and a lower continuous elastic band secured to said outer cup member, and
   said outer cup member formed of a cup-shaped configuration complementarily accepting therein a cup-shaped configuration defined by the exterior surface of said inner cup member, and
   wherein said flange portion includes a plurality of elongate junction hinges to enhance flexibility of said flange portion and accommodate various torso configurations of a wearer.

2. An athletic protective cup apparatus as set forth in claim 1 wherein said inner cup member includes a non-elastic loop secured to a lower terminal end of said inner cup member wherein said inner elastic loop guidingly accommodates said lower elastic band therethrough.

3. An athletic protective cup apparatus as set forth in claim 2 wherein said non-elastic loop further includes an elongate elastic strip secured to said non-elastic loop at one end and secured to a lower terminal end of said outer cup member at its other end.

4. An athletic protective cup apparatus as set forth in claim 3 wherein said outer cup member is formed of a softer material than said inner cup member and is further provided with a fabric covering thereover.

5. An athletic protective cup apparatus as set forth in claim 4 wherein said outer cup member has integrally secured thereto a cushioned perimeter formed about the lowermost portion and sides of said outer cup member.

6. An athletic protective cup apparatus as set forth in claim 5 wherein said inner cup member is removably securable relative to said flange portion by use of snap connector fasteners securing said inner cup member to said flange portion.

7. An athletic protective cup apparatus as set forth in claim 5 wherein said outer cup member further includes a plurality of elongate pockets formed longitudinally of said outer cup member and terminating at an apex proximate a lowermost portion of said outer cup member, and said elongate pockets further include selectively removable flexible strips positionable in said elongate pockets to vary the rigidity of said outer cup member.

* * * * *